United States Patent
Martin (10) Patent No.: US 9,314,238 B2
(45) Date of Patent: Apr. 19, 2016

(54) T-TYPE SUTURE ANCHOR

(75) Inventor: Daniel L. Martin, Palo Alto, CA (US)

(73) Assignee: Syntorr, Inc., Palo Alto, CA (US)

(*) Notice: Subject to any disclaimer, the term of this patent is extended or adjusted under 35 U.S.C. 154(b) by 944 days.

(21) Appl. No.: 12/544,403

(22) Filed: Aug. 20, 2009

(65) Prior Publication Data

US 2010/0114163 A1 May 6, 2010

Related U.S. Application Data

(60) Provisional application No. 61/110,869, filed on Nov. 3, 2008.

(51) Int. Cl.
*A61B 17/04* (2006.01)
(52) U.S. Cl.
CPC ..... *A61B 17/0401* (2013.01); *A61B 2017/0417* (2013.01)
(58) Field of Classification Search
CPC .......... A61B 17/0401; A61B 17/0057; A61B 17/3431; A61B 2017/0409; A61B 2017/0417; A61B 2017/0419; A61B 2017/0414; A61B 2017/042; A61B 2017/06052; A61B 2017/00606; A61B 2017/0061; A61B 2017/00615; A61B 2017/00628; A61B 2017/00641; A61B 2017/346
USPC .......... 606/72, 73, 232, 300, 306; 623/13.13, 623/13.14, 19.11
See application file for complete search history.

(56) References Cited

U.S. PATENT DOCUMENTS

| | | | |
|---|---|---|---|
| 2,008,251 A * | 7/1935 | Hillebrand | 606/146 |
| 4,946,468 A * | 8/1990 | Li | 606/232 |
| 4,968,315 A | 11/1990 | Gatturna | |
| 5,545,180 A * | 8/1996 | Le et al. | 606/232 |
| 5,741,300 A * | 4/1998 | Li | 606/232 |
| 5,879,372 A * | 3/1999 | Bartlett | 606/232 |
| 5,891,168 A * | 4/1999 | Thal | 606/232 |
| 5,961,538 A * | 10/1999 | Pedlick et al. | 606/232 |
| RE36,974 E | 11/2000 | Bonutti | |
| 6,156,056 A * | 12/2000 | Kearns et al. | 606/232 |
| 6,231,561 B1 * | 5/2001 | Frazier et al. | 604/500 |
| 6,436,088 B2 * | 8/2002 | Frazier et al. | 604/508 |
| 6,770,076 B2 * | 8/2004 | Foerster | 606/326 |
| 8,062,334 B2 * | 11/2011 | Green et al. | 606/232 |
| 2002/0128684 A1 * | 9/2002 | Foerster | 606/232 |
| 2005/0075668 A1 | 4/2005 | Lizardi | |
| 2005/0251208 A1 * | 11/2005 | Elmer et al. | 606/232 |
| 2006/0064127 A1 * | 3/2006 | Fallin et al. | 606/232 |
| 2008/0027446 A1 * | 1/2008 | Stone et al. | 606/73 |
| 2008/0071311 A1 * | 3/2008 | White et al. | 606/232 |
| 2008/0281356 A1 * | 11/2008 | Chau et al. | 606/232 |

FOREIGN PATENT DOCUMENTS

| | | |
|---|---|---|
| WO | 96/14798 | 5/1996 |
| WO | 2004/049958 | 6/2004 |

OTHER PUBLICATIONS

PCT Search Report dated Mar. 18, 2010.

* cited by examiner

*Primary Examiner* — Dianne Dornbusch
(74) *Attorney, Agent, or Firm* — Patterson & Sheridan, LLP (57) ABSTRACT

A suture anchor of a T-type is inserted into and through a small-diameter hole formed in a bone and, when deployed, is oriented substantially transversely with respect to the small-diameter hole. Prior to deployment, the suture anchor is coupled to an insertion shaft through a deformable portion and is aligned with the shaft axis so that the insertion shaft and the suture anchor can be inserted into the small-diameter hole.

13 Claims, 14 Drawing Sheets

FIG. 1

PRIOR ART

T-TYPE SUTURE ANCHOR

CROSS-REFERENCE TO RELATED APPLICATION(S)

This application claims the benefit of U.S. Provisional Patent Application Ser. No. 61/110,869, filed Nov. 3, 2008, which is incorporated by reference herein.

BACKGROUND OF THE INVENTION

1. Field of the Invention

Embodiments of the present invention relate generally to medical devices and, more particularly, to devices and methods used in anchoring sutures, e.g., during surgeries involving repair of rotator cuff tendon.

2. Description of the Related Art

Figure 1:
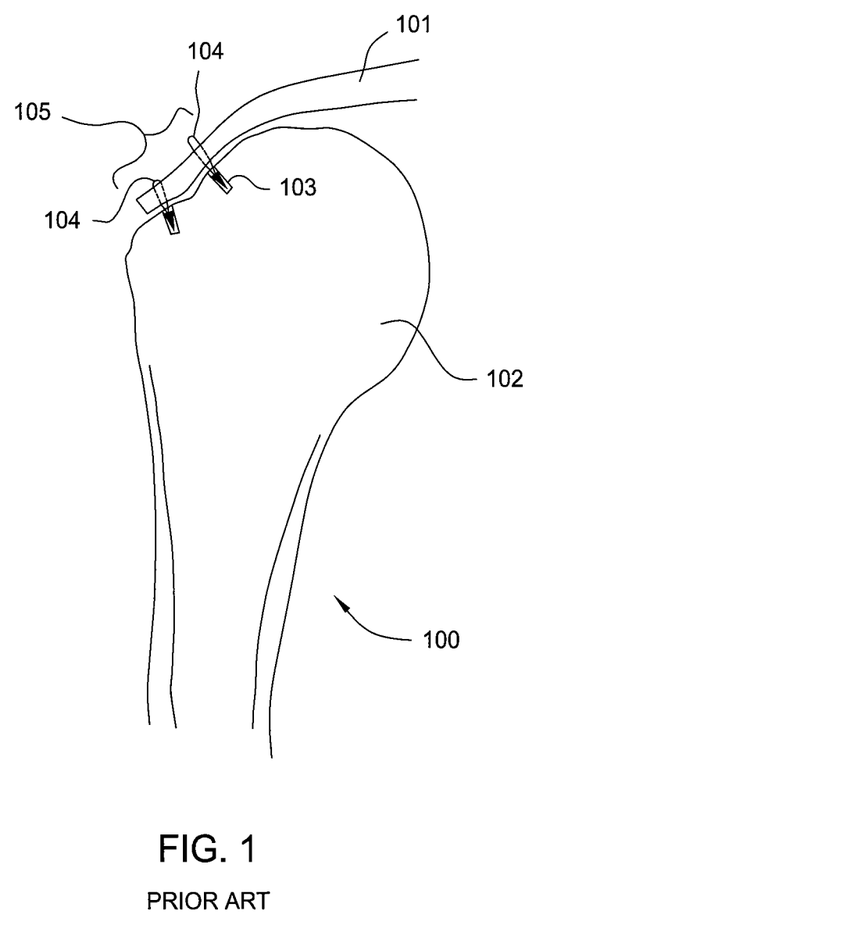
FIG. 1 schematically illustrates a rotator cuff tendon secured to a humeral head of a humerus by a plurality of suture anchors.
Figure 2:
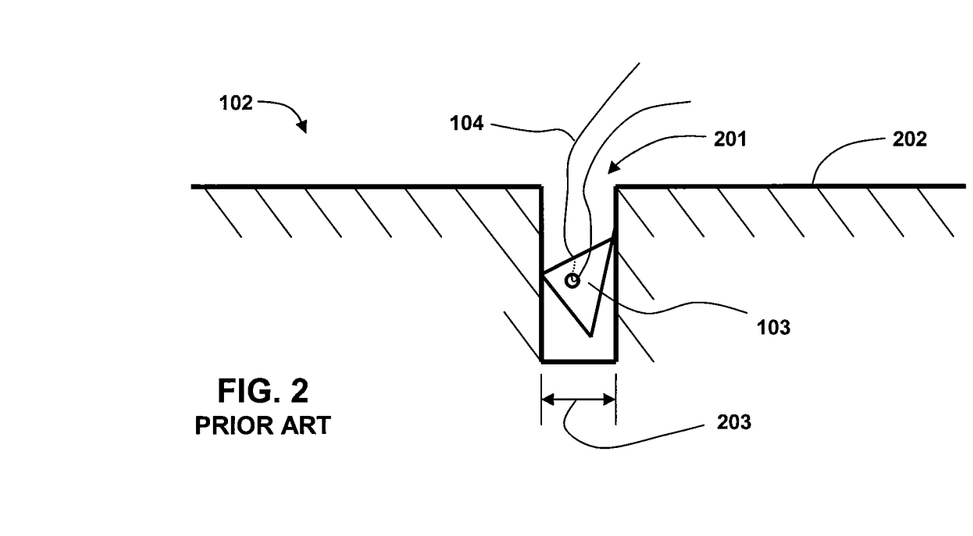
FIG. 2 schematically illustrates one example of a suture anchor known in the art for attaching the rotator cuff tendon.

In surgeries involving repair of a rotator cuff tendon that has been detached from the humeral head, the tendon must be artificially pressed against the humeral head in order to allow the tendon to naturally re-attach to the underlying bone over time. FIGS. 1 and 2 illustrate a prior art technique for repairing a rotator cuff tendon that has been detached from the humeral head.

FIG. 1 schematically illustrates a rotator cuff tendon 101 secured to a humeral head 102 of a humerus 100 by a plurality of suture anchors 103. Suture anchors 103 are positioned so that sutures 104, which are sewn into rotator cuff tendon 101, position the tendon against region 105 of humeral head 102, where region 105 approximates the original anatomic attachment location of rotator cuff tendon 101. In this way, rotator cuff tendon 101 will grow onto region 105, forming a new bond between rotator cuff tendon 101 and humeral head 102. Issues associated with the use of the technique illustrated in FIG. 1 include anchor displacement from the supporting bone, and the availability of only a limited number of sutures for securing rotator cuff tendon 101 to humeral head 102.

FIG. 2 schematically illustrates one example of suture anchor 103 known in the art for attaching the rotator cuff tendon. Suture anchor 103 is positioned in a cylindrical hole 201 formed into the surface 202 of humeral head 102 illustrated in FIG. 1. As illustrated, suture anchor 103 is a wedge-shaped device configured for permanent installation into cylindrical hole 201, where suture anchor 103 can be inserted into cylindrical hole 201 with a pusher rod or other device. Because suture anchor 103 is wedge-shaped, suture anchor 103 is not displaced by the outward force exerted thereon by suture 104 and remains in place throughout the healing process. However, the reliability of suture anchor 103 depends on the material strength of the bone in which cylindrical hole 201 is formed. As long as the bone surrounding suture anchor 103 can withstand the outward force directed on the anchor by suture 104, suture anchor 103 will not be displaced.

It is known that for some patients the bone making up humeral head 102 forms a relatively weak base material for supporting suture anchors, since this portion of humerus 100 is relatively porous and soft. In addition, because the diameter 203 of cylindrical hole 201 is relatively large, typically 3 mm or greater, only a small number of suture anchors 103 can be installed in the appropriate region of humeral head 102, i.e., region 105, using this approach. A smaller number of suture anchors 103 results in higher forces on each suture anchor increasing the possibility that the suture anchor might be displaced out of the hole. Further, the formation of cylindrical holes 201, due to their relatively large diameter 203, can significantly weaken the mechanical strength of the anchoring bone material that surrounds suture anchors 103. Thus, adequate fixation of suture anchors 103 to the weaker bone material of humeral head 102 is problematic, and anchor displacement from the supporting bone is a common failure mechanism of suture anchors 103.

In addition, the use of suture anchors 103 limits the number of sutures securing rotator cuff tendon 101 to humeral head 102. This is due to the size constraint between suture anchors 103 and the region of humeral head 102 in which the anchors are placed. Fewer sutures provide a less robust connection between rotator cuff tendon 101 and humeral head 102. In addition, fewer sutures require the use of larger sutures, which have substantially larger suture and knot volumes. It is known that knots may act as sources of irritation and infection and that knot volume should be minimized, when possible. It is also known that, for a given surgical application, using more small-diameter sutures is generally preferable over fewer large-diameter sutures, since the latter case results in the largest total knot volume. This is because the knot volume of a suture is roughly proportional to the cube of the suture diameter.

Other suture anchors known in the art include devices that screw into cylindrical hole 201 in FIG. 2. Rather than relying on a rotating or "camming" action of the device to remain in place, as described above for suture anchor 103, a screw-in style device is held in place by contact between the external threads of the device and the bone surrounding cylindrical hole 201. This approach also relies on the mechanical strength of the bone surrounding cylindrical hole 201. A stronger mechanical connection between a suture anchoring device and the surrounding bone can be achieved by increasing the diameter of the anchoring device and its associated insertion hole. However, as described above regarding suture anchor 103, forming larger diameter holes in surface 202 of humeral head 102 further weakens the supporting bone and reduces the total number of anchors that can be installed in the desired location. This is particularly problematic for older patients with weaker bones.

SUMMARY OF THE INVENTION

Embodiments of the invention provide devices and methods for anchoring sutures, e.g., during surgeries involving repair of rotator cuff tendon. The suture anchor that is contemplated by one or more embodiments of the invention is of a T-type, which is inserted into a small-diameter hole formed in a bone and, when deployed, is oriented transversely with respect to the small-diameter hole. Prior to deployment, the suture anchor is coupled to an insertion shaft through a deformable portion and is aligned with the shaft axis so that the insertion shaft and the suture anchor can be inserted into the small-diameter hole. Typically, the small-diameter hole is less than 2 mm. In one embodiment, the deformable portion includes a frangible portion that allows deployment of the suture anchor when the frangible portion breaks. In another embodiment, the deformable portion plastically deforms to allow deployment of the suture anchor.

A device for insertion into a bone, according to an embodiment of the invention, includes an elongated shaft portion, a tip portion, and a deformable portion between the elongated shaft portion and the tip portion, wherein a minimum encompassing diameter for the tip portion is large enough to encompass the elongated shaft portion.

A suture anchor, according to an embodiment of the invention, includes a first section having a tip end that terminates at an acute angle and a suture-retaining portion to which one or more sutures are to be affixed and a second section formed integrally with the first section and having a reduced cross-section, wherein the tip end and the reduced cross-section end are at opposite ends of the suture anchor.

A method for anchoring sutures, according to an embodiment of the invention, includes the steps of inserting a device having a shaft portion and a tip portion that has one or more sutures affixed thereto into a bone hole of less than 2 mm in diameter, separating the tip portion from the shaft portion after the device has been inserted into the bone hole, and removing the shaft portion.

BRIEF DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments.

For clarity, identical reference numbers have been used, where applicable, to designate identical elements that are common between figures. It is contemplated that features of one embodiment may be incorporated in other embodiments without further recitation.

DETAILED DESCRIPTION

Embodiments of the invention contemplate a device having a narrow, insertion shaft with a tip, the tip having one or more sutures fixedly attached thereto. The insertion shaft is configured for insertion into a small-diameter hole formed in the surface of the humeral head or other bones so that the tip can be deployed in the humeral head to serve as a suture anchor after the removal of the remainder of the insertion shaft from the small-diameter hole. The tip is separated from the insertion shaft via force exerted parallel to the axis of the insertion shaft and is then deployed in the humeral head. When deployed, the tip is oriented substantially perpendicular to the small-diameter hole formed in the surface of the humeral head, and the suture or sutures fixedly attached thereto exit the external opening of the small diameter hole for attachment to the rotator cuff tendon. In one embodiment, a deformable portion connects the tip to the insertion shaft. The deformable portion may include a frangible portion that allows deployment of the tip when the frangible portion breaks. Alternatively, the deformable portion may plastically deform to allow deployment of the tip. To assist in percutaneous installation of the device into the small-diameter hole formed in the humeral head, a coaxial insertion sheath may be used in conjunction with the insertion shaft.

Figure 3A:
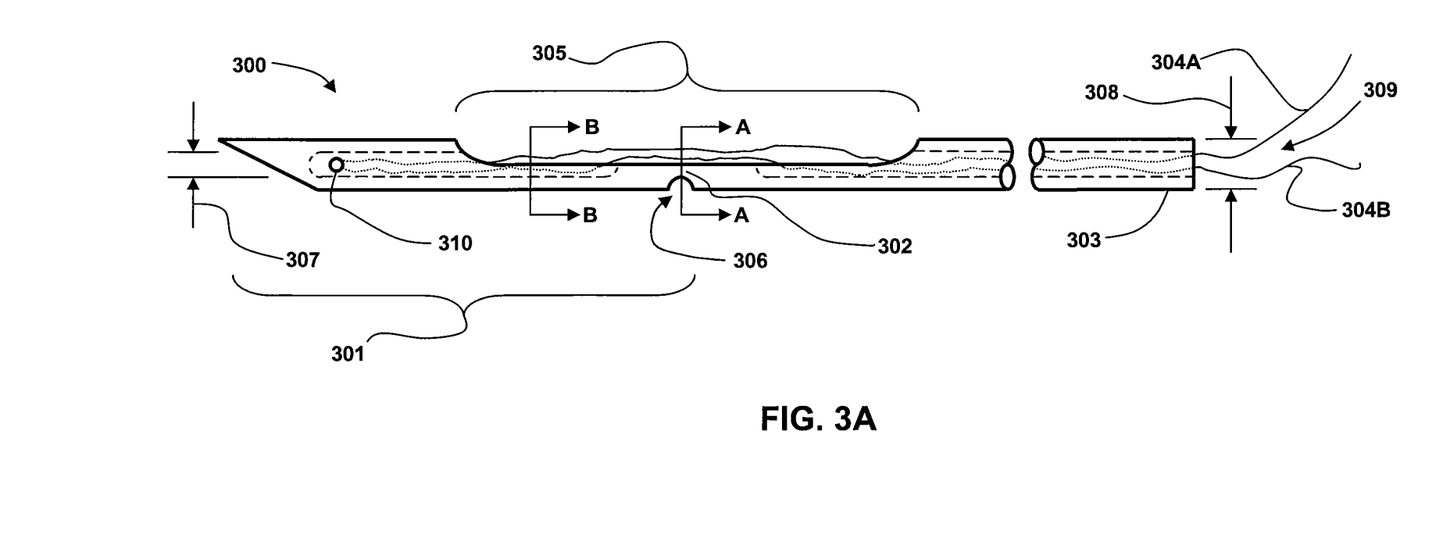
FIGS. 3A depicts a schematic side view of a device having a T-type suture anchor for securing the rotator cuff tendon to the humeral head, according to one embodiment of the invention.

FIG. 3A depicts a schematic side view of a device 300 for securing the rotator cuff tendon to the humeral head, according to one embodiment of the invention. Device 300 includes a removable tip 301, a frangible portion 302, an insertion shaft 303, two suture strands 304A, 304B, and an open channel region 305. Removable tip 301 serves as the T-type suture anchor once separated from insertion shaft 303 and deployed inside the humeral head. In this embodiment, removable tip 301 is substantially similar in configuration to insertion shaft 303, and, prior to deployment in the humeral head, is connected to insertion shaft 303 via frangible portion 302. Removable tip 301 and insertion shaft 303 are formed from a single component, such as a hollow needle constructed of stainless steel or other durable surgical-grade material. The inner diameter 307 of insertion shaft 303 and removable tip 301 is large enough to accommodate at least one strand of suture. The outer diameter 308 of insertion shaft 303 and removable tip 301 is minimized, in order to reduce the amount of bone material removed for the insertion of device 300 into the humeral head, as described below in conjunction with FIG. 4. Outer diameter 308 is contemplated to be as small as about 1 mm, i.e., roughly equivalent to the diameter of a standard 18 gage needle, which can accommodate one or more sutures 304A, 304B. In one embodiment, portions of device 300 may be fabricated from an 18 gage needle.

Figure 3B:
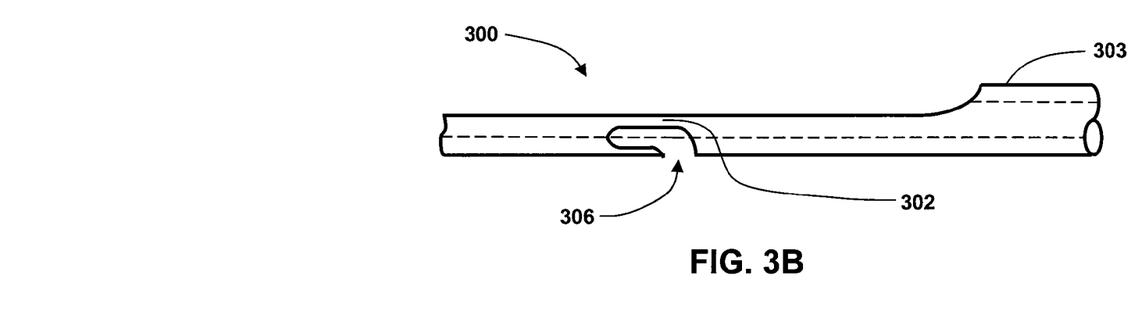
FIG. 3B illustrates a notch configured as a channel-shaped groove according to one embodiment of the invention.

Frangible portion 302 is a portion of device 300 that is substantially weaker mechanically than the other portions of device 300, i.e., frangible portion 302 has a lower yield stress. Thus, when device 300 is subjected to mechanical stress, such as bending moment, frangible portion 302 will plastically deform and break before any other portion of device 300, thereby releasing anchor portion 301 from insertion shaft 303. In this embodiment, frangible portion 302 is formed by a notch 306 disposed on one side of device 300 and open channel region 305, which is disposed opposite notch 306. Notch 306 is illustrated in FIG. 3A as a region of material removed from insertion shaft 303 that is semi-circular in cross-section, as would be the case when formed by a small drill or file. Other configurations of notch 306 are also contemplated. For example, notch 306 may be triangular in cross-section, or, as illustrated in FIG. 3B, notch 306 may be channel-shaped groove. In one embodiment, the cross-sectional area of frangible portion 302 at cross-section A-A is reduced by about 60-90% of the cross-sectional area of anchor portion 301 at cross-section B-B. In this way, frangible portion 302 has enough mechanical strength to allow insertion of device 300, but is substantially weaker than the other portions of device 300. In one embodiment, the length of anchor portion 301 is 5 to 20 times the width of frangible portion 302. Such a configuration further encourages deformation of T-type suture anchor at frangible portion 302 when a force is exerted parallel to the axis of insertion shaft 303 for deployment of anchor portion 301 in the humeral head. Deployment of anchor portion 301 is described below in conjunction with FIG. 3C.

Open channel region 305 is a portion of device 300 in which the outer wall of insertion shaft 303 has been removed to expose the internal channel 309 of device 300. As illustrated in FIG. 3A, open channel region 305 is disposed on both insertion shaft 303 and removable tip 301, and partially defines frangible portion 302. Sutures 304A, 304B are fastened to removable tip 301 at an attachment point 310. Attachment point 310 may be a portion of removable tip 301 that has been swaged onto sutures 304A, 304B. Alternatively, attachment point 310 may be a "necked-down" region in the suture passage hole of removable tip 301. In this embodiment, sutures 304A, 304B are tied together with a knot too bulky to pass through the necked-down region and thus remain fixed to removable tip 301. Other means of attachment for sutures 304A, 304B to attachment point 310 are also contemplated, such as the use of mechanical fasteners or an adhesive inside removable tip 301.

Figure 3C:
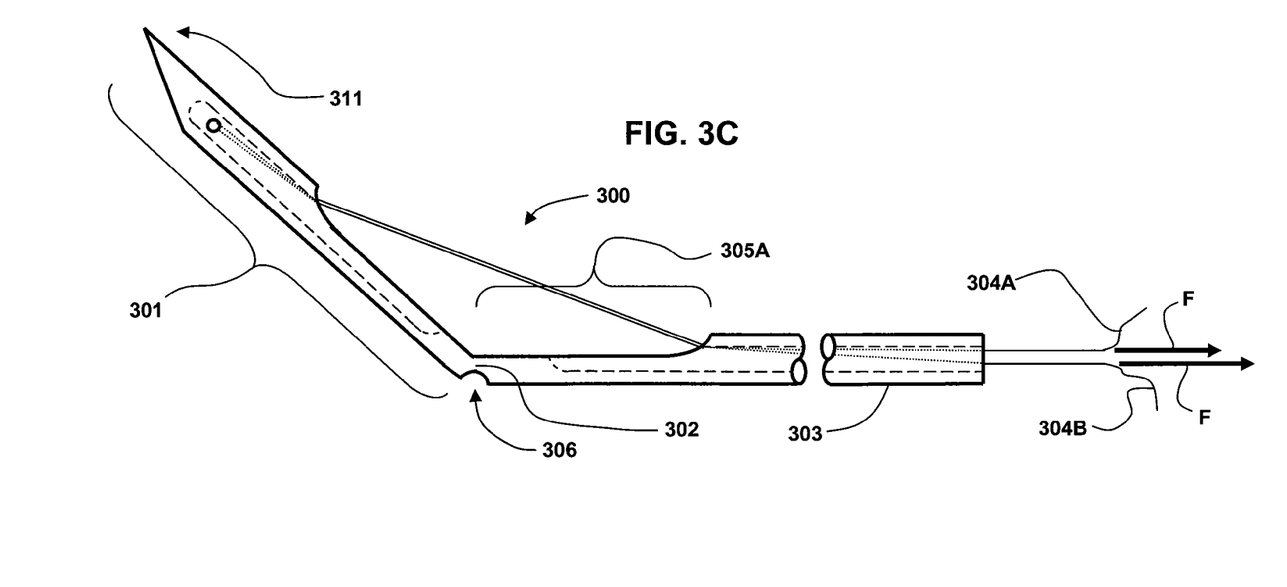
FIG. 3C depicts a schematic side view of a T-type suture anchor, where the removable tip is in the process of being released, according to one embodiment of the invention.

FIG. 3C depicts a schematic side view of device 300, where removable tip 301 is in the process of being deployed, according to one embodiment of the invention. Mechanical stress has been applied to device 300, resulting in plastic deformation of frangible portion 302, as shown. In one embodiment, an axial force F is applied to one or both of sutures 304A, 304B. In another embodiment, point 311 is pressed against a solid surface, such as an inner surface of the humerus. In either case, device 300 hinges at frangible portion 302 due to the substantially weaker yield strength thereof. As the mechanical stress is further applied to device 300, removable tip 301 continues to deflect or bend relative to insertion shaft 303, and frangible portion 302 completely breaks free of insertion shaft 303. Open channel region 305 allows for a greater bending moment to be applied to removable tip 301 when axial force F is applied to one or both of sutures 304A, 304B. The presence of open channel region 305A on insertion shaft 303 reduces the possibility of cutting sutures 304A, 304B on edge 312 of open channel region 305.

Figure 3D:
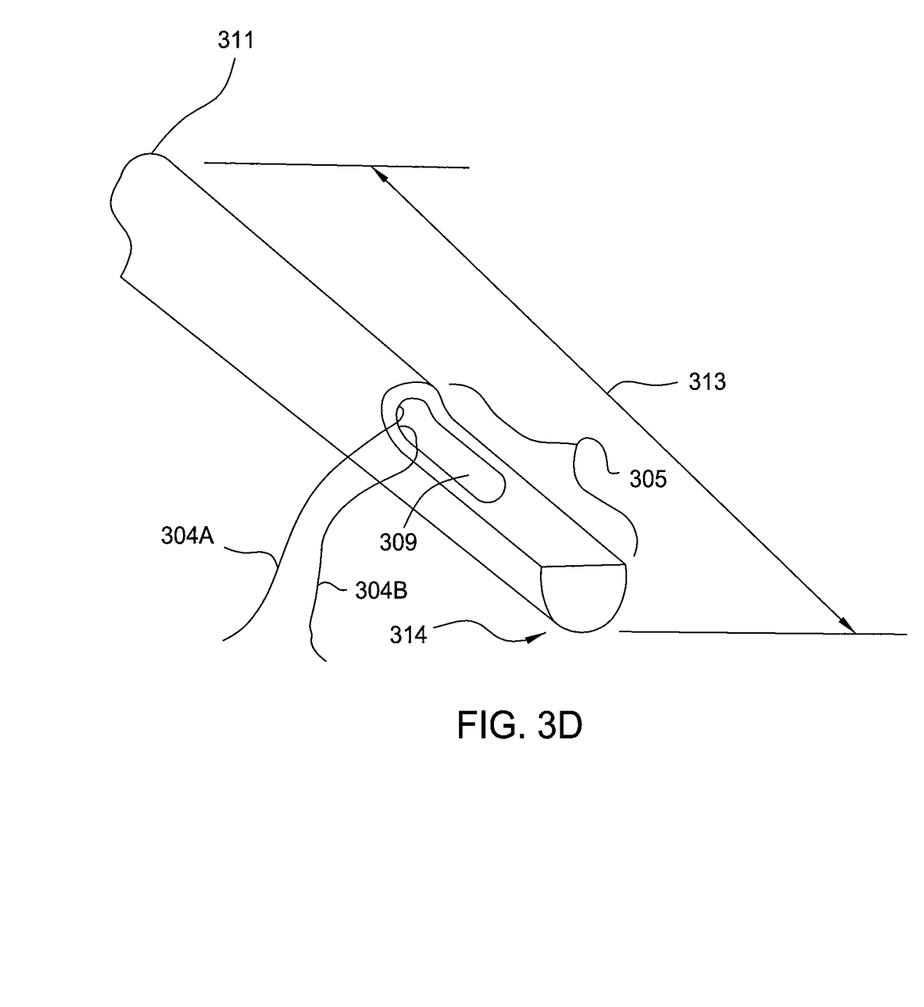
FIG. 3D is an isometric view of a removable tip after being released from a needle-like shaft, according to one embodiment of the invention.

FIG. 3D is an isometric view of removable tip 301 after being separated from insertion shaft 303 in preparation for deployment inside the humeral head. Sutures 304A, 304B exit from internal channel 309 as shown. The portion of open channel region 305 disposed on removable tip 301 is approximately half of length 313 of removable tip 301, so that the exit point of sutures 304A, 304B from internal channel 309 is substantially centered between point 311 and the base 314 of removable tip 301. Thus, when removable tip 301 is separated from insertion shaft 303 and is deployed against an inner surface of the humeral head, removable tip 301 rotates to be substantially orthogonal to sutures 304A, 304B. Removable tip 301 is deployed against the inner surface of the humeral head via tension exerted on sutures 304A, 304B through the insertion opening in the humeral head by the surgeon. In this way, removable tip 301 and sutures 304A, 304B form a "tee," and, hence, removable tip 301 is unable to exit the humeral head through the small diameter insertion opening formed in the humeral head.

Figure 4:
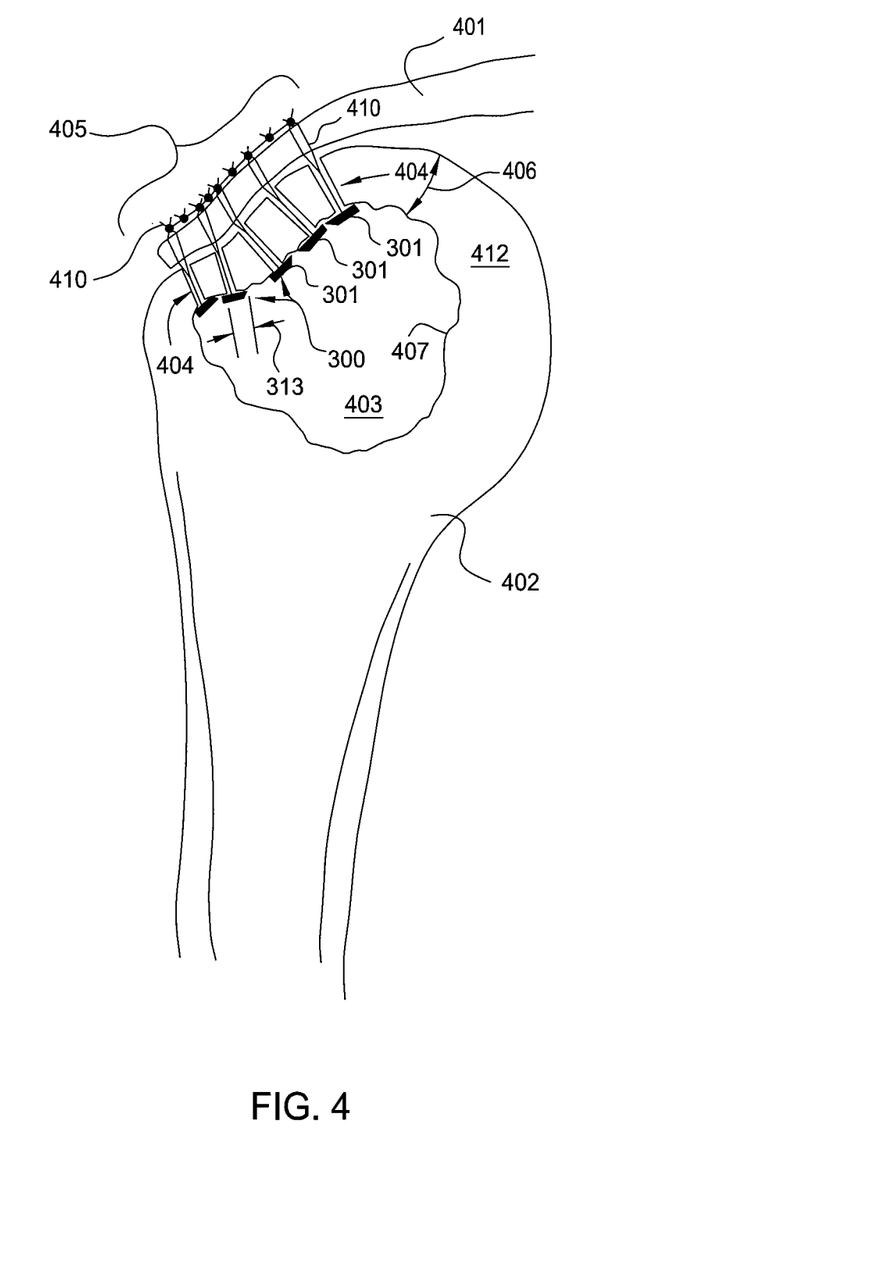
FIG. 4 schematically illustrates a plurality of T-type suture anchors installed in a humeral head and securing a rotator cuff tendon thereto, according to one embodiment of the invention.

FIG. 4 schematically illustrates a plurality of T-type suture anchors installed in a humeral head 402 and securing a rotator cuff tendon 401 thereto, according to one embodiment of the invention. In patients with weaker humeral bone, humeral head 402 is often substantially hollow, having a cavity 403 of substantially softer and weaker material disposed therein. It is understood that "substantially hollow" refers to a region of significantly harder and/or denser bone material surrounding a region of significantly softer and/or less dense material, rather than a completely void-like region. As shown, removable tip 301 has been separated from insertion shaft 303 (shown in FIGS. 3A, 3B) after device 300 has been inserted into humeral head 402, and deployed against an inner surface 407 of cavity 403. To accomplish this, removable tip 301 and a portion of insertion shaft 303 of device 300 are inserted into cavity 403 via an insertion opening 404, which is a small-diameter hole drilled or otherwise formed in humeral head 402. Each insertion opening 404 is made as small as possible, but large enough to allow passage of insertion shaft 303 with removable tip 301 mounted thereon through the surface bone of humeral head 402 and into cavity 403. For clarity, the width of insertion openings 404 in FIG. 4 is exaggerated relative to the thickness 406 of humeral bone 412 and length 313 of removable tips 301. Removable tips 301 are separated by either pulling on sutures 410 after removable tip has been inserted into cavity 403 or by pressing removable tip 301 against internal surface 420 of cavity 403, thereby causing disengagement of removable tip 301.

As shown, rotator cuff tendon 401 is held against region 405 of humeral head 402, where region 405 approximates the original anatomic attachment location of rotator cuff tendon 401. Each removable tip 301 which serves as T-type suture anchor in FIG. 4 is fastened to one or more sutures 410, which may be sewn into rotator cuff tendon 401 and/or tied together, or the collective sutures may be passed to a different point of fixation. For clarity, a relatively small number of T-type suture anchors are illustrated in FIG. 4, however, it is contemplated that many more T-type suture anchors, e.g., 10-30, can be installed in region 405 of humeral head 402 than depicted.

Thus, suture anchor displacement due to weak supporting material is avoided and more robust and anatomic positioning of rotator cuff tendon 401 can be achieved. First, insertion openings 404 are relatively small in diameter, i.e., about 2 mm, and therefore do not significantly weaken the mechanical strength of humeral bone 412 when compared to 3 mm and larger diameter suture anchors. Second, each suture anchor, i.e., each removable tip 301, contacts a relatively large portion of inner surface 407. Compared to a suture anchor installed in an opening formed in humeral bone 412, each removable tip 301 does not depend on the mechanical strength of the small portion of humeral bone 412 in which the opening is formed. Instead, each removable tip 301 relies on the mechanical strength of the entire thickness 406 of humeral bone 412. Third, since a large number of suture anchors can be installed in region 405, the maximum force distributed to each T-type suture anchor is substantially lower than when a smaller number of prior art anchors are used. In addition, the larger number of suture anchors installed in region 405 allows smaller diameter sutures to be used compared to prior art suture anchors. For example, a plurality of #0 sutures may be used in place of a small number #2 or #5 sutures. Lastly, the large number of anchors that can be installed in region 405 allows optimal positioning of rotator cuff tendon 401 against region 405 for the most anatomic surgical result.

Figure 5:
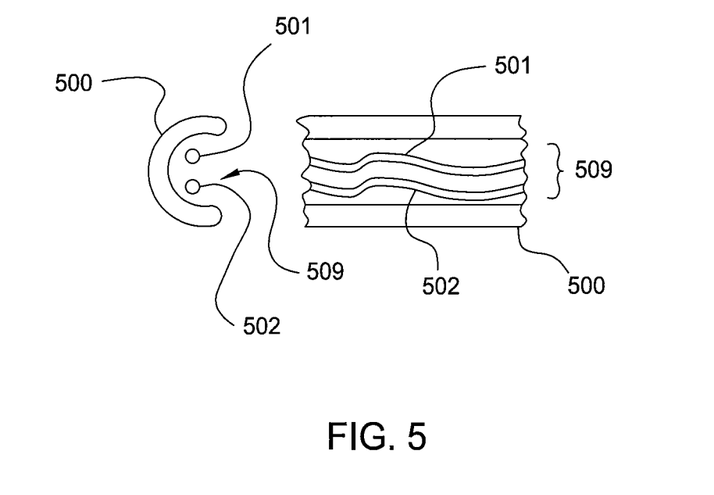
FIG. 5 schematically illustrates an end view and a partial side view of an insertion shaft having an internal channel that is not fully enclosed, according to an embodiment of the invention.

A device having a T-type suture anchor may also have alternative configurations according to the present invention. FIG. 5 schematically illustrates an end view and a partial side view of a insertion shaft 500 having an internal channel 509 that is not fully enclosed, according to an embodiment of the invention. Suture 501, 502 are contained in internal channel 509 as shown, but because internal channel 509 is an open channel formed in insertion shaft 500, sutures 501, 502 do not have to be threaded through the length of insertion shaft 500 prior to insertion in the humeral head. In addition, when this configuration of insertion shaft 500 is used, the chances of sutures 501, 502 being cut can be reduced when a removable tip, such as removable tip 301 in FIGS. 3A, 3B, is separated from insertion shaft 500.

Figure 6:
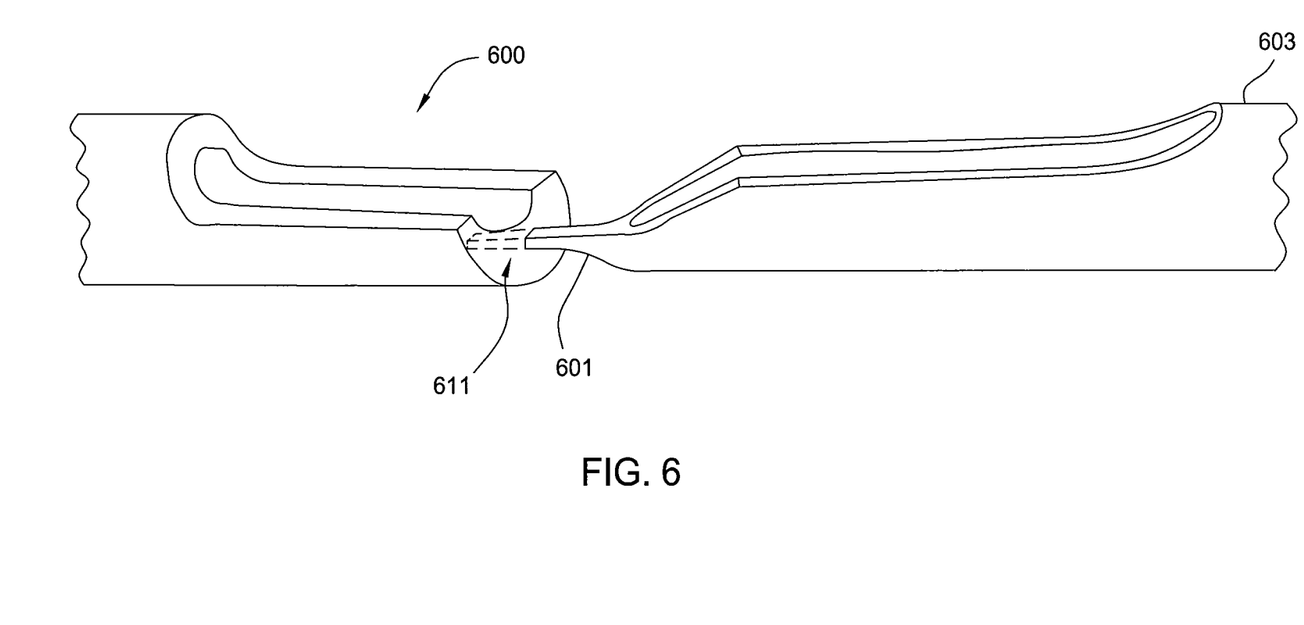
FIG. 6 is a partial isometric view of a removable tip and a frangible connector, according to an embodiment of the invention.

In another embodiment, a device having a T-type suture anchor includes a removable tip, an insertion shaft, and a deformable connector between the removable tip and the insertion shaft. FIG. 6 is a partial isometric view of a removable tip 600 and a deformable connector 601, according to an embodiment of the invention. Removable tip 600 is a separate component from both deformable connector 601 and the insertion shaft 603. Removable tip 600 is fabricated from stainless steel, PEEK or other durable surgical-grade material and includes an attachment point for one or more sutures and a retaining slot 611 for deformable connector 601. Deformable connector 601 is configured to press-fit into retaining slot 611 formed in removable tip 600. The size of deformable connector 601 is selected to ensure that the yield strength thereof is substantially less than the yield strength of any other portion of the device, thereby ensuring that removable tip 600 will be separated when sufficient bending moment is applied to the device containing removable tip 600. In one embodiment, deformable connector 601 is rectangular in cross-section and is fabricated from the same material as the insertion shaft. The diameter of removable tip 600 is approximately 1-2 mm, and the height and width of frangible connector 601 is about 0.008 inches and about 0.020 inches, respectively.

Figure 7:
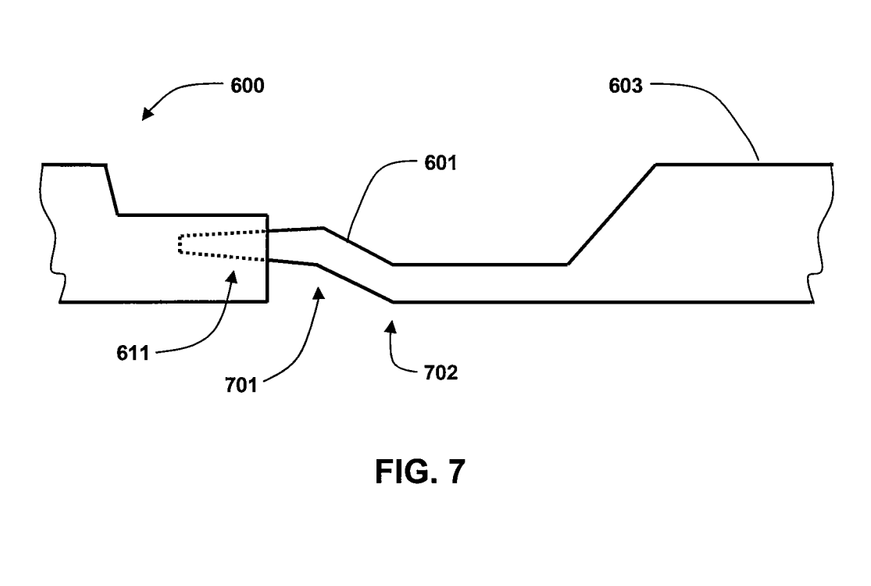
FIG. 7 illustrates a schematic side view of a deformable connector with a double elbow configuration according to an embodiment of the invention.

In another embodiment, deformable connector 601 plastically deforms to better allow the separation of removable tip 600 from insertion shaft 603. Deformable connector 601 may include a double elbow configuration, as illustrated in FIG. 7. FIG. 7 illustrates a schematic side view of deformable connector 601 with a double elbow configuration. Deformable connector 601 includes two elbows 701, 702. When removable tip 600 is pressed against a solid surface, such as an inner surface of the humerus, elbows 701 and/or 702 may plastically deform to the point that removable tip 600 will slip out of retaining slot 611 as removable tip 600 is pressed against the solid surface.

In the embodiments illustrated in FIGS. 6 and 7, deformable connector 601 inserts into a corresponding slot of removable tip 600. In alternative embodiments, the deformable connector may be integral with the removable tip and a slot for receiving the deformable connector may be formed in the insertion shaft.

Figure 8A:
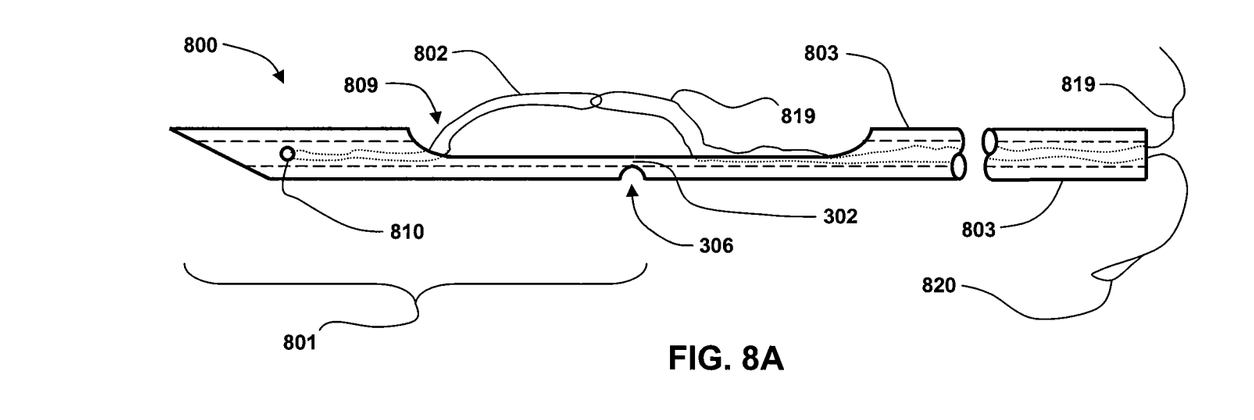
FIGS. 8A-C illustrate partial schematic side views of a device that includes a T-type suture anchor with a suture loop, according to embodiments of the invention.
Figure 8B:
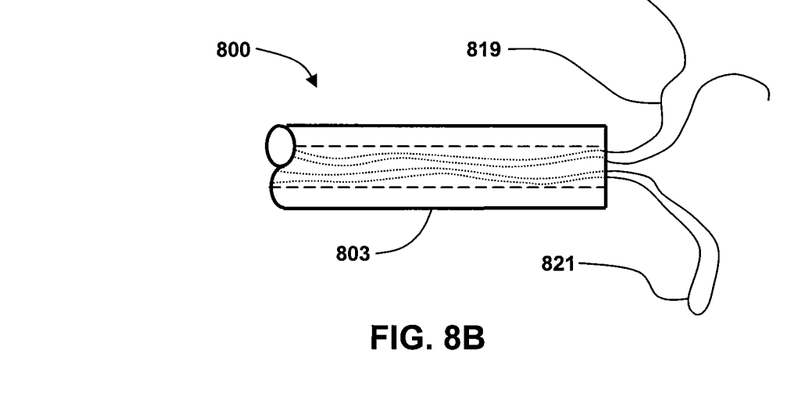
Figure 8C:
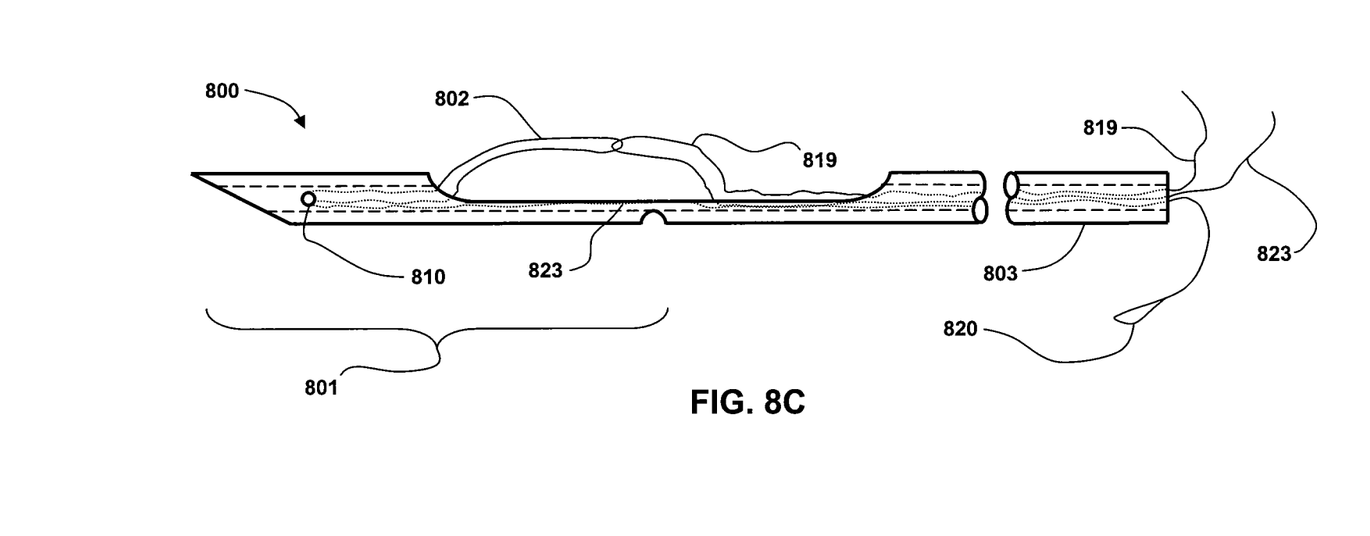

When tying sutures that are sewn into a rotator cuff tendon, the ability to adjust the position of the knot is advantageous for the surgeon. In one embodiment, the sutures fastened to a T-type anchor form a loop rather than one or more individual strands. An additional suture can then be fed through the loop and sewn through the rotator cuff tendon and tied. In this way, the tightness of the suture knot can be easily adjusted by the surgeon by sliding one arm of the suture through a partially tied knot. FIG. 8A illustrates a partial schematic side view of a device 800 that includes a removable tip 801 with a suture loop, according to an embodiment of the invention. Removable tip 801 is similar in configuration to removable tip 301 in FIGS. 3A, 3B. Unlike removable tip 301, however, removable tip 801 does not have individual strands fastened thereto. Instead, a suture loop 802 is fastened to removable tip 801 at an attachment point 810 and an additional suture loop 819 is fed through suture loop 802 as shown. For clarity, suture loop 802 and additional suture loop 819 are illustrated partially removed from the internal channel 809 of removable tip 801. It is understood that suture loop 802 and additional suture loop 819 are preferably disposed inside internal channel 809 during insertion of device 800 into the humeral head. To serve as a passing suture, additional suture loop 819 may be a single strand having a braided loop 820 formed at the end thereof, which is positioned external to device 800 and the humerus for ready access by the surgeon. Alternatively, additional suture loop 819 may be made up of two strands of a conventional suture to form a loop 821 positioned external to device 800, as illustrated in FIG. 8B, thereby serving as a passing suture. In this embodiment, a total of four strands are fed through the insertion shaft 803 of device 800, and the inner diameter of insertion shaft 803 is sized accordingly. In yet another embodiment, removable tip 801 may include both a suture loop 802 and one or more individual suture strands 823 fastened to attachment point 810, as illustrated in FIG. 8C. One skilled in the art will readily appreciate the distinct advantages of each configuration of device 800 as described herein when deployed in the humeral head.

In order to form insertion openings for T-type suture anchors described herein, the surface of the humeral head may be exposed in a conventional manner. Because the extensive dissection of soft tissue that such an approach requires leads to high morbidity, the present invention contemplates the use of T-type suture anchors in conjunction with an insertion sheath, both for the percutaneous formation of insertion openings in the humeral head and for the insertion of T-type suture anchors into the insertion openings.

Figure 9A:
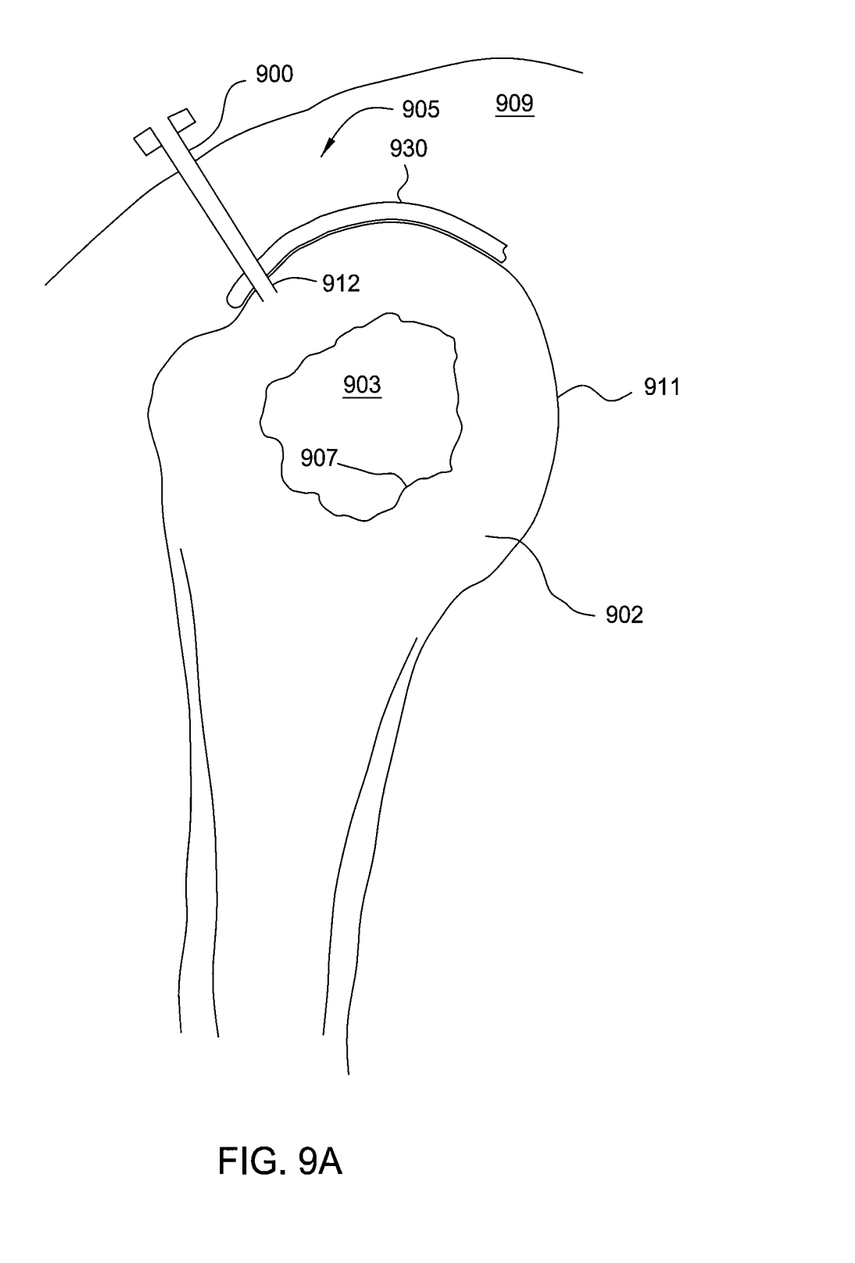
FIG. 9A schematically illustrates an insertion sheath penetrating the soft tissue overlying a region of a humeral head to which a rotator cuff tendon will be sutured, according to an embodiment of the invention.
Figure 9B:
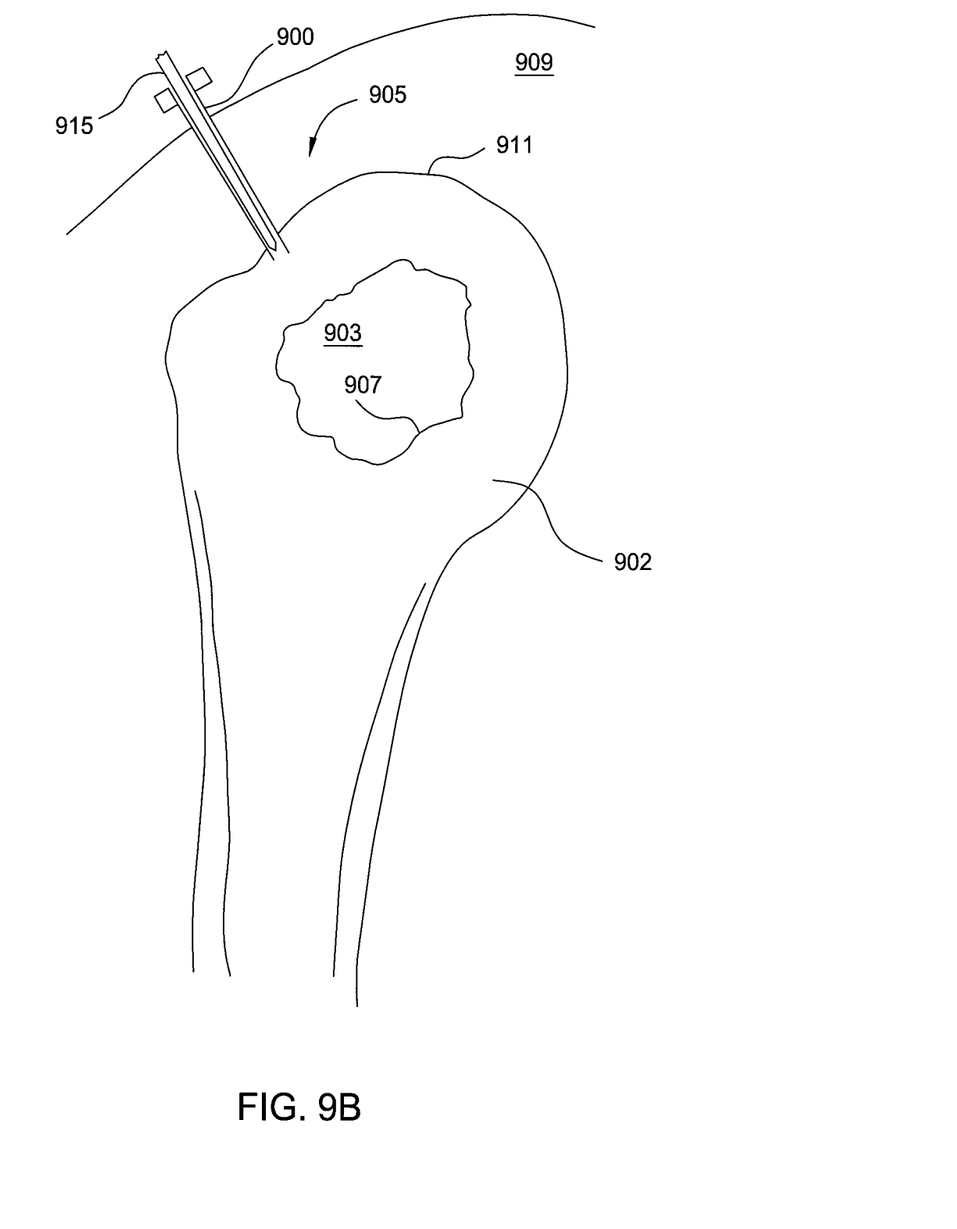
FIG. 9B schematically illustrates a drill bit positioned inside an insertion sheath and used to form an insertion opening in a humeral head for a device having a T-type suture anchor as described herein.
Figure 9C:
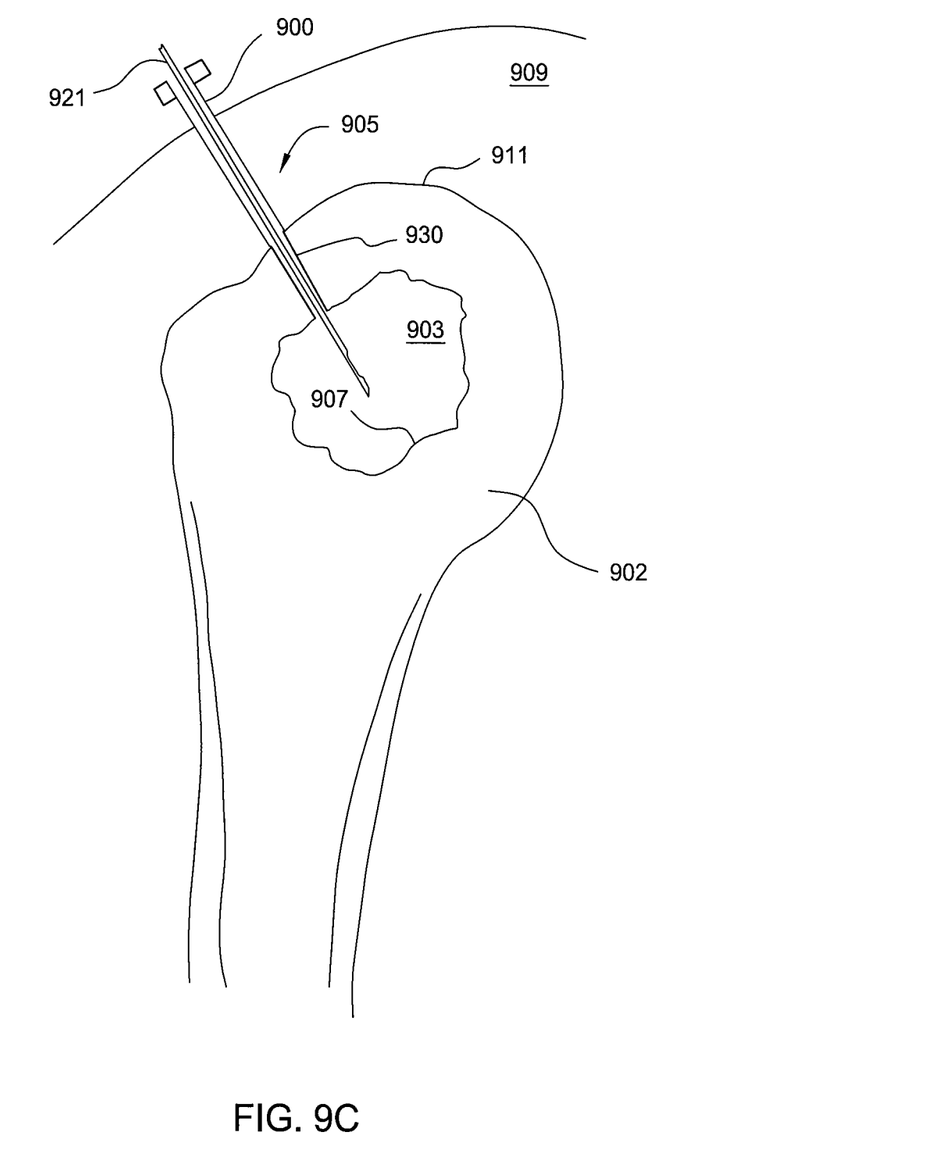
FIG. 9C schematically illustrates a device having a T-type suture anchor positioned in an insertion sheath and an insertion opening prior to deployment of the T-type suture anchor.

FIG. 9A schematically illustrates an insertion sheath 900 penetrating the soft tissue 909 overlying a region 905 of a humeral head 902 to which a rotator cuff tendon 930 will be sutured, according to an embodiment of the invention. FIG. 9B schematically illustrates a drill bit 915 positioned inside insertion sheath 900 and used to form an insertion opening 930 in humeral head 902 for a T-type suture anchor as described herein. FIG. 9C schematically illustrates a device 921 having a T-type suture anchor positioned in insertion sheath 900 and insertion opening 930 prior to separation of the T-type suture anchor from device 921.

Figure 10:
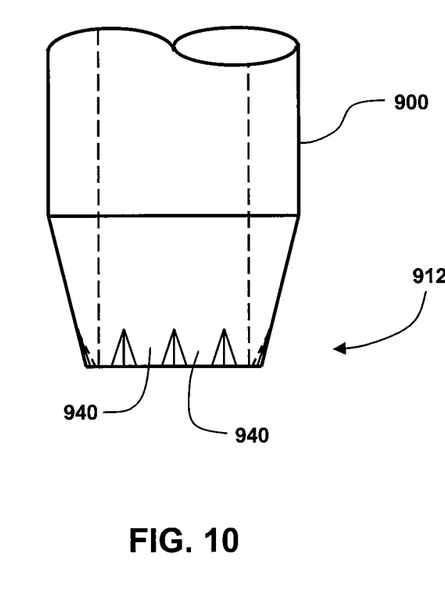
FIG. 10 illustrates the tip of an insertion sheath, according to an embodiment of the invention.

Insertion sheath 900 is configured to have an inner diameter sized to accommodate a T-type suture anchor and insertion shaft as described herein and an outer diameter that is only as large as necessary for insertion sheath 900 to have adequate mechanical strength as required. In one embodiment, insertion sheath 900 is configured to be strong enough for penetration of soft tissue 909. For example, the inner diameter of insertion sheath 900 may be about 1.1 mm, to accommodate an 18 gage T-type suture anchor, and the outer diameter of insertion sheath 900 may be about 1.3 times the inner diameter. In another embodiment, insertion sheath 900 is configured to be strong enough to slightly penetrate the surface 911 of humeral head 902, in which case the outer diameter of insertion sheath may be increased. In this embodiment, the tip 912 of insertion sheath 900 may also be configured with cutting teeth 940, illustrated in FIG. 10, to encourage penetration of surface 911 by insertion sheath 900.

In operation, insertion sheath 900 is advanced through soft tissue 909 until in contact with surface 911, as illustrated in FIG. 9A. In order to reduce the forward force required to advance insertion sheath 900 through soft tissue 909, drill bit 915 may be fed through insertion sheath 900 and used to form a passage into soft tissue 909. In this embodiment, both insertion sheath 900 and drill bit 915 may be mechanically coupled to a drilling device, using a bayonet lock or other mounting method, and rotated together. In this way, drill bit 915 and insertion sheath 900 are advanced together as a unitary component into soft tissue 909. As noted above, insertion sheath 900 may also be advanced into surface 911 slightly, e.g., 2 or 3 mm. In this embodiment, insertion sheath 900 serves as a more stable drill guide for drill bit 915, as illustrated in FIG. 9B. After insertion sheath 900 is positioned as desired, drill bit 915 is then inserted into insertion sheath 900 and used to form insertion opening 930. After the formation of insertion opening 930, drill bit 915 is withdrawn and device 921 is inserted through insertion sheath 900 so that the removable tip of device 921 can be deployed inside humeral head 902. Endoscopic inspection may be used at this time to confirm that device 921 is positioned correctly prior to deployment of the removable tip. The removable tip can be deployed by pulling sutures fastened thereto, or by pressing the removable tip against inner surface 907 of substantially hollow region 903 inside humeral head 902. Thus an additional advantage of the invention, as described herein, is the ability to percutaneously install T-type anchors in the humeral head, minimizing dissection and subsequent morbidity of soft tissue overlying the humeral head.

While the foregoing is directed to embodiments of the present invention, other and further embodiments of the invention may be devised without departing from the basic scope thereof, and the scope thereof is determined by the claims that follow.

What is claimed is:

1. A device for insertion into a bone cavity, comprising:
    an elongated body extending in a longitudinal direction between a first end by which the device is to be inserted into the bone cavity, and a second end opposite to the first end in the longitudinal direction, the elongated body including first and second portions, a deformable portion between the first and second portions, and an internal channel that extends along a center of the elongated body in the longitudinal direction from the second end toward the first end and past the deformable portion, the first end rotating with respect to the second portion by bending at the deformable portion and then separating from the second portion, when the first end comes into contact with an inner surface of the bone cavity,
    wherein the first portion extends in the longitudinal direction between the first end and the deformable portion, and the second portion extends in the longitudinal direction between the second end and the deformable portion, and
    wherein the first portion has an outer wall that is removed partially to expose the interior channel near the deformable portion, and the second portion has an outer wall that is removed partially to expose the interior channel near the deformable portion.

2. The device of claim 1, wherein the exposed interior channel on the side of the first portion is continuous with the exposed interior channel on the side of the second portion.

3. The device of claim 2, wherein the exposed interior channel on the side of the first portion extends about half of an entire longitudinal length of the first portion.

4. The device of claim 3, wherein the first portion has a suture-retaining portion to which one or more sutures that are to be passed through the internal channel are to be affixed, the suture-retaining portion being located closer to the first end than the deformable portion.

5. The device of claim 1, wherein a minimum encompassing diameter for the tip portion is large enough to encompass the elongated shaft portion.

6. The device of claim 1, wherein the first end of the elongated body terminates at an acute angle.

7. The device of claim 6, wherein the first end of the elongated body is not axisymmetric.

8. The device according to claim 1, wherein a cross-sectional area of the deformable portion is 60-90% of that of a portion of the first portion adjacent to the deformable portion.

9. The device according to claim 1, wherein a cross-sectional area of the reduced cross-section is 60-90% of that of a portion of the second portion adjacent to the deformable portion.

10. The device according to claim 1, wherein a length of the first portion is 5 to 20 times a width of the deformable portion.

11. The device according to claim 1, wherein a diameter of the second portion is about 1 mm.

12. The device according to claim 1, wherein the deformable portion is a frangible portion, and the first portion separates from the second portion by breaking off from the second portion as a result of bending at the frangible portion.

13. The device according to claim 1, wherein the first portion separates from the second portion by slipping out of engagement with the second portion when the first portion is rotated with respect to the second portion.

* * * * *